United States Patent [19]
Finter et al.

[11] 4,012,198
[45] Mar. 15, 1977

[54] IMMUNODIFFUSION DEVICE

[75] Inventors: Norman Boyne Finter, Sevenoaks; Leonard William Jerome Bishop, Beaconsfield; June Dalziel Almeida, London, all of England

[73] Assignee: Burroughs Wellcome Co., Raleigh, N.C.

[22] Filed: Feb. 27, 1975

[21] Appl. No.: 553,692

Related U.S. Application Data
[63] Continuation of Ser. No. 381,228, July 20, 1973, abandoned.

[30] Foreign Application Priority Data
July 25, 1972 United Kingdom ............ 34643/72

[52] U.S. Cl. .......................... 23/253 R; 23/230 B; 195/127
[51] Int. Cl.² ........................................ G01N 31/02
[58] Field of Search ....... 23/253 R, 253 TP, 230 B; 195/103.5 R, 127, 139; 204/180 G; 424/12

[56] References Cited
UNITED STATES PATENTS

| | | | |
|---|---|---|---|
| 3,389,966 | 6/1968 | Saravis ........................ | 23/253 R X |
| 3,725,004 | 4/1973 | Johnson et al. .............. | 23/253 R X |
| 3,736,100 | 5/1973 | Rains ............................ | 23/253 R |
| 3,740,196 | 6/1973 | Stroterhoff .................... | 23/253 TP |

*Primary Examiner*—Norman Yudkoff
*Assistant Examiner*—Barry I. Hollander
*Attorney, Agent, or Firm*—Donald Brown

[57] ABSTRACT

A device for use in carrying out immunodiffusion having a trough for accommodating a substrate and one or more wells in communication with the trough whereby a first immunological reagent when located in said well may diffuse into the substrate to react with a second immunological reagent dispersed in said substrate.

1 Claim, 5 Drawing Figures

IMMUNODIFFUSION DEVICE

This is a continuation of application Ser. No. 381,228, filed on July 20, 1973, now abandoned.

The present invention relates to immunodiffusion (ID), and in particular to a device for use in immunodiffusion tests.

ID is a well-known immunological technique. In one application, immuno-double-diffusion, antigens and antibodies diffuse each from a separate reservoir (usually known as a well) through a substrate which has been gelled by the addition of agar. Where a sufficient concentration of an antigen and an appropriate antibody interact in the substrate, precipitation may occur, and this can be seen as a line or band. In another application, single radial immuno-diffusion, antigen is incorporated in the gelled substrate, and an appropriate antibody diffusing from a well into the substrate gives rise to an annular zone of precipitate (or conversely, antibody is incorporated in the substrate and antigen diffuses from a well into the substrate; see also below at p. 6 line 23 to p. 7 line 3).

As used herein a "substrate" is any medium in which ID may be successfully effected. Thus a substrate is usually a substantially transparent gel, for example, agar or agarose, gelatin, pectin, cellulose acetate, starch, crosslinked dextran, or a chemical which polymerises to a gel when a catalyst is added to an aqueous solution of the chemical, e.g. acrylamide. The substrate optionally contains one or more salts and/or buffers, conventional in the art of immunodiffusion. Salts and buffers are usually chosen to give a pH from 6.5 to 8.2 and an ionic strength of from 0.05 to 0.025 mol/Kg. Suitable concentrations of buffers are from 0.2 to 0.05 M. Conventional buffers include phosphate buffers, barbital, TRIS, and ethylene diaminetetraacetic acid. A suitable salt is sodium chloride of which a suitable concentration is of the order of 0.85% w/v NaCl.

ID tests are carried out in a number of ways. Until now, they have usually been carried out in a chamber with a glass or plastic base on which there is a thin layer of gelled substrate. Wells are formed in the substrate by removing cylinders of agar, and the antigens and antibodies are introduced into these wells.

One disadvantage of such a system is the difficulty of producing accurately located wells of consistent dimensions without disturbing the surrounding gel medium, and it is an object of the present invention to provide a device for carrying out ID in which this and other disadvantages are reduced or overcome.

It is a further object of the present invention to provide a device which affords a greater degree of sensitivity than is obtainable with conventional systems.

It has now been found that ID can be readily and advantageously performed using a container having a well, for accommodating an immunological reagent, which is preformed in the structure of the container, the well being in communication with the trough of the container through a conduit which allows diffusion of the reagent into a substrate layer present in the trough.

The arrangement of the well(s), conduit(s), and the chamber (or trough) in the device and the configuration of the well(s), chamber, and conduit(s) are all readily variable and are chosen as those being most suitable for the particular type of ID to be carried out. Nevertheless certain arrangements and configurations afford additional advantages. For example, in one embodiment the configuration of the chamber in the vicinity of the conduit forms a 180° sector having its origin at the conduit. However, any sector less than 360° is suitable and affords an increase in sensitivity over conventional systems wherein diffusion from a well in the substrate itself takes place in a 360° sector. The increase in sensitivity accrues from the directing of diffusion within the sector and thus predominantly in the direction required. The directing of diffusion has the effect that, since the diffusion of antigen from the well is concentrated into a smaller volume of substrate, a smaller total quantity of antigen is required in order to produce a given concentration of antigen in the substrate, for example a concentration sufficient to form an immunoprecipitate with a corresponding antibody. Furthermore, less substrate is required to fill a sector less than 360° than is required for a 360° sector. Thus use of such configurations results in economies in both reagent and substrate materials.

A device of the present invention may be made from any rigid impermeable material, though a plastic material is preferred. Especially preferred, however, is a translucent or transparent material as this permits viewing of immunoprecipitates in the substrate when illuminated from below. Suitable materials include glass and plastic materials such as polyacrylates, for example, clear 'Perspex' (Trade Name).

In use of a device of the present invention for single radial ID, liquefied substrate is introduced into the chamber and when the substrate has solidified, a corresponding antigen is introduced into one or more wells from which it diffuses through the conduits into the substrate in the chamber. If the antibody is present in a suitable concentration in the substrate, then an immunoprecipitate will form where a suitable antigen-antibody concentration ratio obtains.

In the course of introduction of liquefied substrate into the chamber and prior to solidification of the substrate therein, it is necessary to prevent a flow of substrate into the well(s) through the conduit(s). This object may be readily achieved by occluding the well and/or the conduit with a removable plug. One example of a suitable plug is a sleeve which fits into the well so as to obscure the opening of the conduit into the well.

Alternatively, the configuration of the conduit may be chosen so that although reagent can pass therethrough, a more viscous liquefied substrate cannot pass. For example, in the case of liquefied agar at 40° C, if the configuration of the conduit is a slit having a width of the order of 0.1 mm., the liquefied agar does not pass through the conduit into the well whereas immunological reagents can readily pass through such a slit and thence diffuse into the substrate. The maximum width of the conduit which will prevent passage of liquefied substrate will of course vary with the nature of the substrate and the temperature thereof and any other factors that affect the flow properties of the liquefied substrate.

Whether or not the conduit is of the type that prevents the passage of substrate, the configuration of the conduit may take one of a number of different forms. For example, the conduit may be a channel or a bore in a side wall of the chamber, and of any cross section consistent with permitting a flow of reagent through it and consistent with the nature of the material from which the body of the device is made. Furthermore, the configuration of the conduit may be variable along its length, for example, the conduit may have a constriction. Naturally in such a case the flow of liquefied substrate and/or reagent through the conduit will be determined by the width of the conduit at the constriction. Advantageously, the conduit is of the same depth as the well to allow a maximum diffusion of reagent therethrough.

Desirably a device of the present invention is provided with a lid. The lid may be used in the course of storage of a device of the present invention where the chamber is filled with substrate, in order to protect the substrate from contamination and to minimise dehydration of the substrate, and in such a case the lid is advantageously closely fitting. The lid may also be used to protect the substrate from contamination in the course of immunodiffusion. Advantageously the lid covers both the chamber and the well(s).

In the context of the present invention antigen and antibody are readily interchangable and either may be described as an immunological reagent. The expression 'corresponding' when applied to any of antigen, antibody, and immunological reagent is used in the sense that a material is capable of forming, with a corresponding material, an immunoprecipitate. Thus, for example, an antibody that has been raised against an antigen or a related antigen is a corresponding antibody to that antigen in so far as it is capable of forming an immunoprecipitate with that antigen.

When reference is made to antibody or antigen, for example, the introduction thereof into wells, such references should normally be construed as references to antibody or antigen in solution. Nevertheless the present invention also applies to those causes where antigen or antibody other than in solution, for example, as a freeze-dried preparation, is introduced into a well and reconstituted with water therein so as to give a solution of the antigen or antibody in the well. Conveniently antigen or antibody solution may be introduced into a well, dried therein and subsequently reconstituted.

The present invention provides a device comprising a body having a chamber preferably but not necessarily of substantially uniform depth and at least one well in the body in communication with said chamber through a conduit.

In another aspect the present invention provides a device comprising a body having a chamber preferably though not necessarily of substantially uniform depth and at least one well in the body in communication with said chamber through a conduit, said chamber having a layer of a substrate therein the edge of which can contact a solution of reagent when introduced into the well.

In yet another aspect the present invention provides a device comprising a body having a chamber preferably though not necessarily of substantially uniform depth and at least one well in the body in communication with said chamber through a conduit, said chamber having a layer of a substrate having dispersed therein an immunological reagent, the edge of the substrate being capable of contacting a solution of reagent when introduced into the well.

In a further aspect the present invention provides a device comprising a body having a chamber preferably though not necessarily of substantially uniform depth and at least one well in the body in communication with said chamber through a conduit, said chamber being filled with a substrate, one or more of the wells containing freeze-dried immunological reagent.

The following is a description by way of example only of two devices in accordance with the present invention, in which.

Figure 1:
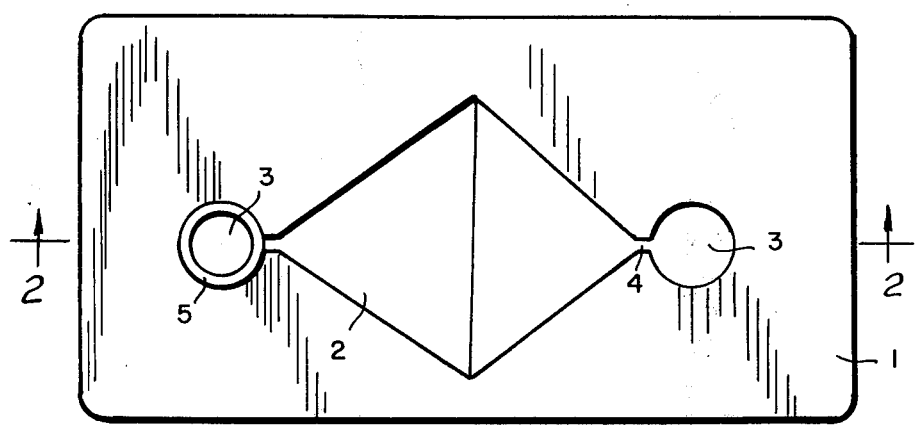
FIG. 1 shows a plan view, of the first embodiment.
Figure 2:
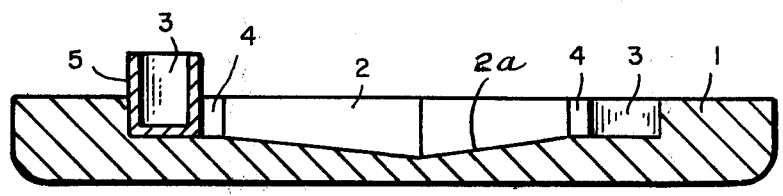
FIG. 2 shows a sectional elevation of FIG. 1, along the line 2—2.

The immunodiffusion device of FIGS. 1 and 2 comprises a body 1, chamber 2, and wells 3 in communication with chamber 2 through conduits 4. The angle between the side walls defining the chamber 2 is preferably less than 90° and greater than 45°.

In FIGS. 1 and 2, one of the wells 3 is occluded by a removable plug 5 in the form of a sleeve closed at one end which has a depth greater than that of the well 3.

The chamber 2 is generally lozenge-shaped and has a 'V' shaped floor 2a. The conduits 4 are located in opposed corners at the vertices of sectors, each of less than 90°.

In use of the device, the removable plug 5 is inserted closed end first into both of the wells 3, and sufficient liquefied substrate is introduced into the chamber 2 to substantially fill it. When the substance has solidified, the plugs 5 are withdrawn from the wells 3 into one of which is then poured antigen and into the other antibody, taking care not to fill either of the wells above the level of the substrate.

The antigen and antibody then diffuse through the conduits 4 into the substrate and towards one another until a sufficient concentration of each obtains whereupon an immunoprecipitate forms.

Figure 3:
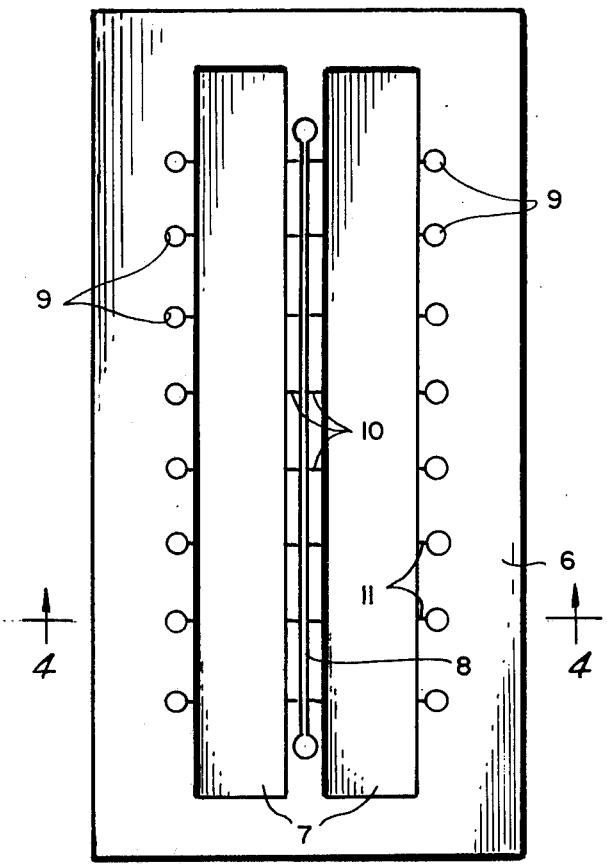
FIG. 3 shows a plan view of the second embodiment.
Figure 4:
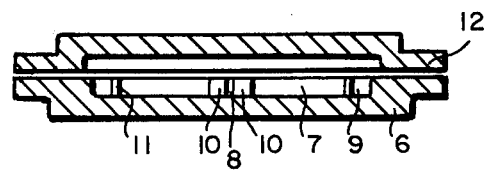
FIG. 4 shows a sectional elevation of FIG. 3 along the line 4—4 together with a lid not shown in FIG. 3.
Figure 5:
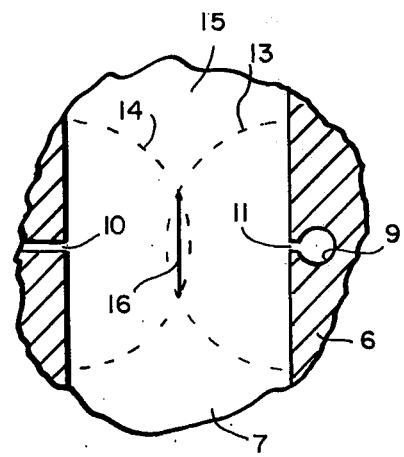
FIG. 5 shows a detail plan view of the device of FIG. 3 in use.

The device of FIGS. 3, 4, and 5 comprises a body 6, having two substantially parallel and rectangular chambers 7, a central well 8, and two sets of outer wells 9. The central well 8 is located between the chambers 7 and communicates with each of the chambers 7 through a plurality of substantially equally-spaced inner conduits 10. Each of the outer wells 9 communicates with one of the chambers 7 through an outer conduit 11 which is disposed opposite one of the inner conduits 10.

The device is also provided with a lid 12 which covers the chambers 7 and the wells 8 and 9.

Each of the conduits 10 and 11 is in the form of a vertical slit narrow enough to prevent the flow of liquefied substrate from a chamber into a well.

In use of the device of FIGS. 4, 5, and 3, liquefied substrate is poured into each of the chambers 7 and when the substrate has solidified, antibody is introduced into the central well 8 and antigen into each of the outer wells 9; for example, a mixture of antibodies is introduced into the central well 8 and a different antigen or different concentrations of the same antigen is introduced into each of the outer wells 9, and the lid 12 placed over the body 6.

The antigen and antibody diffuse into 180° sectors 13 and 14 respectively in the substrate 15 and where a suitable concentration ratio of antigen and antibody obtains, an immunoprecipitate band 16 forms.

In a third embodiment (not shown), the central well 8 of the second embodiment is replaced by a plurality of central wells, each of the central wells being in communication with each of the chambers 7 through an inner conduit 10.

In a fourth embodiment, the chamber 2 of the first embodiment is of substantially uniform depth and the wells 3 are square in cross-section.

What we claim is:

1. A device suitable for use in carrying out immunodiffusion comprising a container having a base wall and side walls, said walls defining therebetween two parallel troughs for accommodating a substrate, a slit in the body of the container extending between said two troughs, a plurality of channels extending from said slit to said troughs, and a plurality of wells and conduits located in the side walls of said container corresponding to each of said channels whereby a immunological reagent placed in said slit would diffuse into a substrate located in each of said troughs via a channel and combine in said substrate with an homologus immunological reagent having diffused into said substrate from corresponding conduit and well.

* * * * *